United States Patent
Golan et al.

(10) Patent No.: US 9,192,738 B2
(45) Date of Patent: Nov. 24, 2015

(54) DEVICES AND METHODS FOR CRIMPING MEDICAL DEVICES

(71) Applicant: Medtronic Vascular Galway Limited, Ballybrit, Galway (IE)

(72) Inventors: Saar Golan, Netanya (IL); Tal Gollan, Netanya (IL); Daniel Glozman, Netanya (IL)

(73) Assignee: Medtronic Vascular Galway, Ballybrit, Galway (IE)

(*) Notice: Subject to any disclaimer, the term of this patent is extended or adjusted under 35 U.S.C. 154(b) by 249 days.

(21) Appl. No.: 13/785,191

(22) Filed: Mar. 5, 2013

(65) Prior Publication Data
US 2013/0283596 A1    Oct. 31, 2013

Related U.S. Application Data

(60) Provisional application No. 61/637,942, filed on Apr. 25, 2012.

(51) Int. Cl.
| | |
|---|---|
| *A61M 25/00* | (2006.01) |
| *A61F 2/95* | (2013.01) |
| *A61F 2/24* | (2006.01) |
| *A61F 2/91* | (2013.01) |

(52) U.S. Cl.
CPC .............. *A61M 25/0009* (2013.01); *A61F 2/95* (2013.01); *A61F 2/2418* (2013.01); *A61F 2/91* (2013.01); *A61F 2002/9522* (2013.01); *Y10T 29/49908* (2015.01); *Y10T 29/53996* (2015.01)

(58) Field of Classification Search
CPC .................. A61M 25/009; A61F 2/95; A61F 2002/9522; A61F 2/2418; Y10T 29/49908; Y10T 29/53996

USPC ............................................................ 72/402
See application file for complete search history.

(56) References Cited

U.S. PATENT DOCUMENTS

| | | | | |
|---|---|---|---|---|
| 3,800,386 | A | * | 4/1974 | Bishop ..................... 29/890.132 |
| 3,822,456 | A | * | 7/1974 | Petruzzi .......................... 29/871 |
| 4,261,194 | A | * | 4/1981 | Stephens ......................... 72/402 |
| 5,634,367 | A | * | 6/1997 | Yamada et al. ................. 72/402 |
| 6,058,755 | A | * | 5/2000 | Viegener ......................... 72/292 |
| 6,237,389 | B1 | * | 5/2001 | Tada et al. ....................... 72/402 |
| 6,618,921 | B1 | * | 9/2003 | Thornton ......................... 29/270 |
| 7,530,253 | B2 | | 5/2009 | Spenser et al. |
| 7,914,569 | B2 | | 3/2011 | Nguyen et al. |
| 8,099,851 | B2 | * | 1/2012 | Roach et al. .................... 29/516 |
| 8,631,671 | B2 | * | 1/2014 | Krajewski et al. ................ 72/62 |
| 8,904,846 | B2 | * | 12/2014 | Mader et al. .................... 72/402 |
| 2005/0044924 | A1 | * | 3/2005 | Dole ............................... 72/402 |
| 2006/0259136 | A1 | | 11/2006 | Nguyen et al. |
| 2008/0071363 | A1 | | 3/2008 | Tuval et al. |
| 2012/0101569 | A1 | | 4/2012 | Mearns et al. |

\* cited by examiner

*Primary Examiner* — Edward Tolan (57) ABSTRACT

A crimping device used with a medical device can include at least one force-applying surface configured to compress the medical device by applying a force to a surface of the medical device. The crimping device also includes at least one protruding element extending from the force-applying surface and arranged to least partially extend into one of the openings defined by frame struts while the medical device is being crimped. The extension of the at least one protruding element at least partially into one of the openings prevents at least a portion of the soft layer of the medical device from protruding between struts of the outer frame of the medical device while the device is being crimped.

17 Claims, 11 Drawing Sheets

DEVICES AND METHODS FOR CRIMPING MEDICAL DEVICES

CROSS-REFERENCE TO RELATED APPLICATION

This application claims the benefit of U.S. Provisional Application No. 61/637,942, filed Apr. 25, 2012, which is incorporated herein by reference.

FIELD

Embodiments of the present invention generally relate to medical devices. Specifically, embodiments relate to devices and methods for crimping a medical device to facilitate placement of the medical device in a subject's body.

BACKGROUND

Medical devices, for example, stents, prosthetic valves, and other implantable medical devices, can be compressed to facilitate delivery of the devices at an implantation site in a subject's body, for example, a native cardiac valve. The medical devices are delivered to the implantation site via a delivery device (for example, a catheter) having radial dimensions that are smaller than the unconstrained or expanded radial dimensions of the medical device (i.e., the radial dimensions of the medical device, when the medical device is in an unconstrained state), and/or that are smaller than the dimensions of the medical device upon deployment of the medical device at the implantation site, a native cardiac valve. To facilitate insertion of such a medical device into or on the delivery device, the medical device is compressed (typically, at least radially).

BRIEF SUMMARY

In some embodiments, a crimping device is used with a medical device. The medical device includes a frame that has struts defining openings, and includes a soft layer coupled to the frame. The crimping device includes at least one force-applying surface configured to compress the medical device by applying a force to a surface of the medical device. The crimping device also includes at least one protruding element extending from the force-applying surface and arranged to at least partially extend into one of the openings defined by the struts while the medical device is being crimped. The extension of the at least one protruding element at least partially into one of the openings prevents at least a portion of the soft layer of the medical device from protruding between struts of the outer frame of the medical device while the device is being crimped.

In some embodiments, a method for crimping a medical device includes compressing the medical device by applying a force to an outer surface of the medical device with a force-applying surface. The medical device includes a frame that comprises struts defining openings, and includes a soft layer coupled to the frame. The method also includes inserting at least one protruding element that extends from the force-applying surface at least partially into one of the openings defined by the struts while the medical device is being compressed to prevent at least a portion of the soft layer of the medical device from protruding between the struts of the frame of the medical device.

In some embodiments, a crimping system can be used with a medical device. The medical device includes a frame having struts that define openings, and includes a soft layer coupled to the frame. The crimping system includes a crimping device. The crimping device includes at least one force-applying surface configured to compress the medical device by applying a force to a surface of the medical device. The crimping system also includes a support member configured to be operatively coupled to the medical device while the force-applying surface applies a force to the surface of the medical device. The support member includes at least one protruding element extending from a surface of the support member and arranged to at least partially extend into one of the openings defined by the struts while the crimping device crimps the medical device. The extension of the at least one protruding element at least partially into one of the openings prevents at least a portion of the soft layer of the medical device from protruding between struts of the outer frame of the medical device while the device is being crimped.

DETAILED DESCRIPTION

Figure 1:
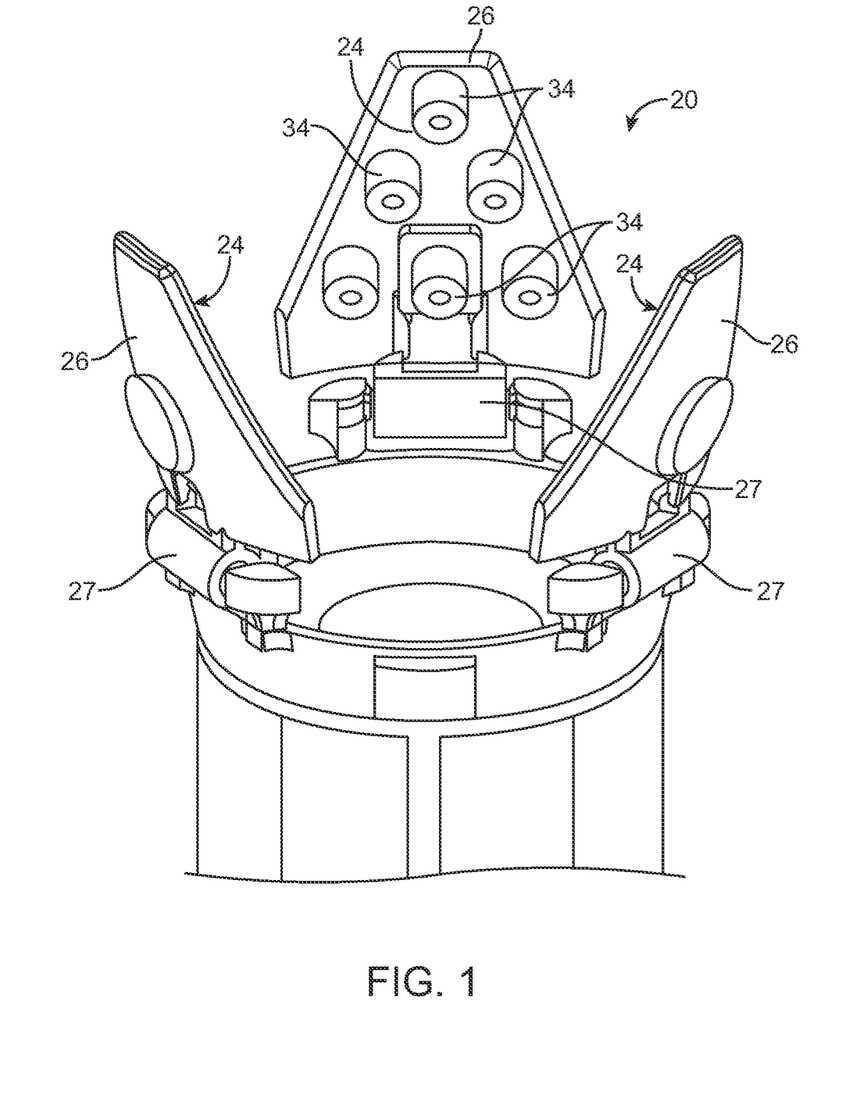
FIGS. 1-3 are schematic illustrations of a winged crimping device according to an embodiment.
Figure 2:
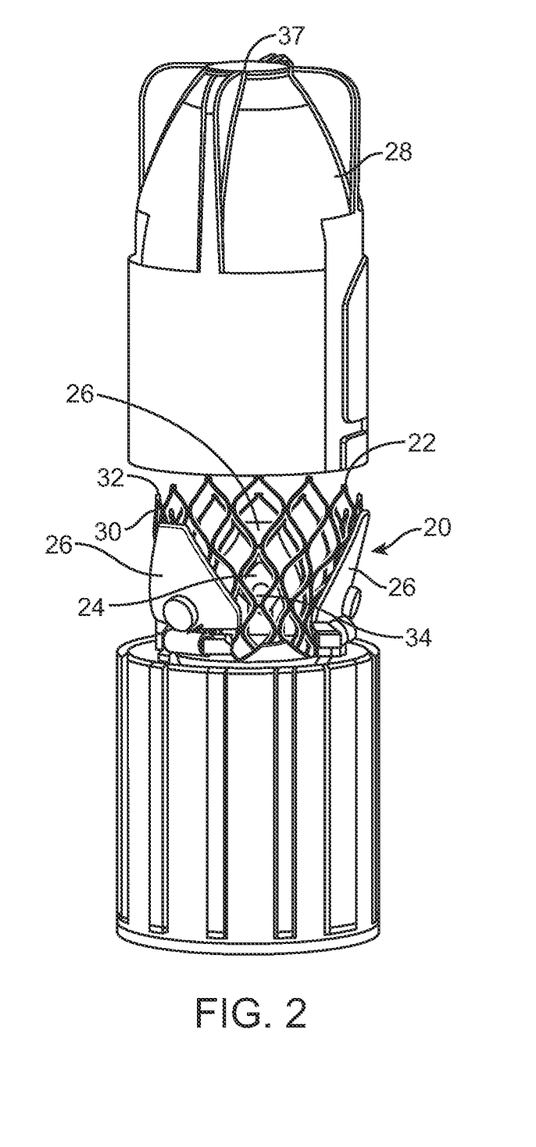
Figure 3:
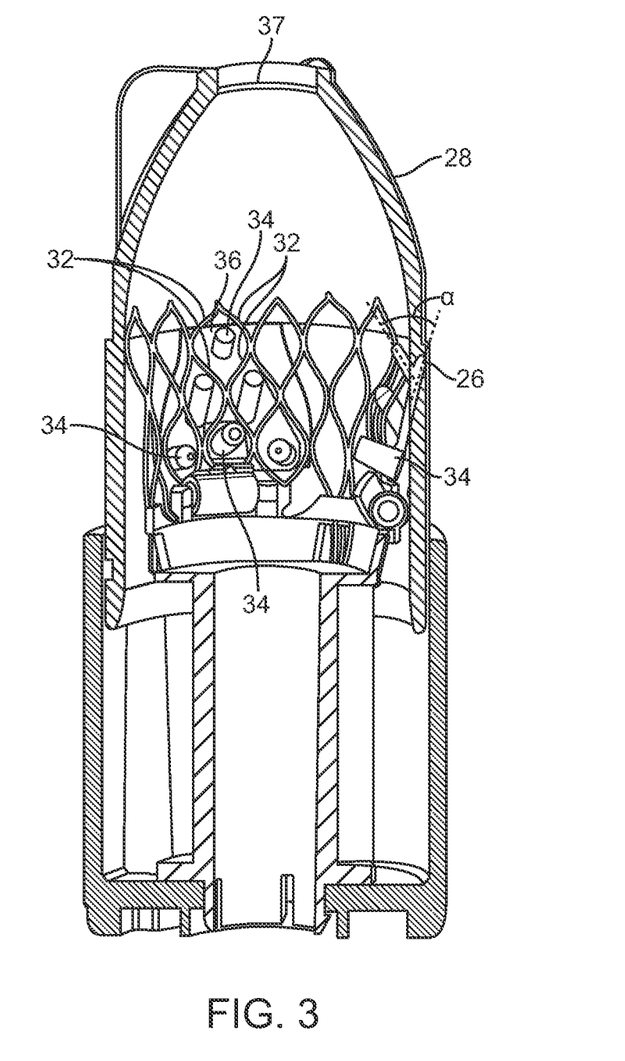

Referring to FIGS. 1-3, which are schematic illustrations of a winged crimping device 20, according to an embodiment, for use with a medical device 22. Medical device 22 can be any medical device that can be compressed to facilitate delivery of the device at an implantation site in a subject's body. For example, medical device 22 can be a stent, prosthetic valve, or any other implantable medical device.

In some embodiments, medical device 22 includes a soft layer (not shown in FIGS. 1-3), for example, a soft inner lining such as a skirt that surrounds the periphery of medical device 22, and/or prosthetic valve leaflets. Medical device 22 can also include a frame 30 (shown in FIG. 2) that comprises struts 32. In some embodiments, the soft layer can be a polymer, such as a polyurethane, polytetrafluoroethylene, or polydimethylsiloxane; a polyester; any other suitable biocompatible synthetic material; biological pericardial tissue; synthetic pericardial tissue; or any other suitable biological material. In some embodiments, frame 30 can be rigid. Frame 30 can be made of a metal, for example, cobalt chromium; nickel molybdenum; iron alloy; tantalum; 316L steel; a shape-memory alloy, such as nitinol; or any other suitable metal. In some embodiments, medical device 22 can be a prosthetic valve that includes a soft lining, soft prosthetic valve leaflets, and frame 30. For example, medical device 22 can be a prosthetic valve as described in U.S. Patent Application Publication No. 2008/0071363 to Tuval et al. or U.S. Patent Application Publication No. 2006/0259136 to Nguyen et al.

In some embodiments, struts 32 can define one or more openings 36. For example, struts 32 can form a plurality of diamond shaped openings 36 that uniformly define the circumferential body of frame 30. In at least some of the embodiments, the diamond shaped openings 36 have a different size and/or shape at the inflow end and at the outflow end of frame 30 of medical device 22. In some embodiments, a central portion between the inflow end and the outflow end of frame 30 has diamond shaped openings 36 of a third size and/or shape to form a medical device 22 having a narrowed central portion. The soft layer of medical device 22 is coupled to frame 30 using any suitable attachment method, for example, suturing. In some embodiments, the soft layer axially overlaps with at least portions of one or more openings 36 defined by struts 32. In some embodiments, the soft layer is coupled to an outside surface of frame 30. In some embodiments, the soft layer is coupled to an inside surface of frame 30. In some embodiments, medical device 22 can include one or more soft layers. For example, medical device 22 can be a prosthetic valve comprising a soft skirt layer coupled to the inside or outside of frame 30, and one or more prosthetic valve leaflets coupled to the inside or outside of frame 30. Medical device 22 can be crimped to facilitate delivery of device 22 to an implantation site in a subject's body.

Crimping device 20 may include one or more wings 26. For example, as shown in FIGS. 1-3, crimping device 20 may include three wings 26. Crimping device 20 is configured to crimp (i.e., compress) medical device 22 by applying one or more forces to the medical device with a force-applying surface 24 of wings 26 of crimping device 20. In some embodiments, crimping device 20 radially compresses medical device 22 by applying inward radial forces to medical device 22 with force-applying surfaces 24. Crimping device 20 applies the radial forces to medical device 22 as medical device 22 and crimping device 20 are moved through a compression funnel 28 (shown in FIGS. 2 and 3), which causes wings 26 of crimping device 20 to constrict and apply radial forces to medical device 22 with force-applying surfaces 24. Wings 26 can be configured to pivot such that crimping device 20 can be constricted. For example, wings 26 can be configured to pivot about pivot assemblies 27. In some embodiments, pivot assemblies 27 can be a hinge as shown in FIGS. 1-3.

In some embodiments, crimping device 20 can also include at least one protruding element 34 disposed on one or more of force-applying surfaces 24. For example, as shown in FIGS. 1-3, crimping device 20 can include a plurality of protruding elements 34 disposed on each force-applying surface 24. Protruding elements 34 can be shaped to at least partially, and in some embodiments fully, extend into an opening 36 defined by struts 32 of the frame 30 during at least a portion of a period during which force-applying surfaces 24 applies radial forces to medical device 22—when medical device 22 is operatively coupled with crimping device 20. In some embodiments, one or more of openings 36 in which protruding elements 34 extend axially overlap with a soft layer (e.g., a soft lining and/or prosthetic valve material such as prosthetic valve leaflets) of medical device 22. In some embodiments, protruding elements 34 are sized to be smaller than openings 36 of frame 30. For example, as shown in FIG. 1-3, protruding elements 34 can have a circular cross-sectional shape that is sized to fit within the diamond-shaped openings 36 of medical device 22. In some embodiments, protruding elements 34 can have a non-circular cross-sectional shape, for example, a diamond, oval, polygonal, or any other suitable cross-sectional shape, that is sized to fit within openings 36 of frame 30. In some embodiments, protruding elements 34 are cylindrical. In some embodiments, protruding elements 34 have a non-cylindrical shape, for example, a conical, hemispherical, parabolic, hyperbolic, elliptical, or any other suitable non-cylindrical shape. In some embodiments, protruding elements 34 are rigid. Protruding elements 34 can be made of a plastic, a biocompatible polymer (such as polyurethane and/or polyethyleneimine), a silicone-based material, or any other suitable material.

Protruding elements 34 can be configured to prevent at least a portion of a soft layer (not shown in FIGS. 1-3) of medical device 22 (e.g., a soft inner lining and/or prosthetic valve leaflets), which axially overlaps with openings 36 of frame 30, from protruding between struts 32 of outer frame 30 of medical device 22, while the force-applying surfaces 24 apply forces to medical device 22—while medical device 22 is being crimped. In some embodiments, protruding elements 34 can reduce damage to the soft layer of the medical device that may result from the soft layer protruding between openings 36 defined by struts 32 while the device is crimped.

In some embodiments, winged crimping device 20 can be used with compression funnel 28 as shown in FIGS. 1-3. Medical device 22 is placed inside crimping device 20, and crimping device 20 and medical device 22 are then pulled towards an outlet 37 at one end of compression funnel 28. Pulling crimping device 20 and medical device 22 towards outlet 37 of compression funnel 28 causes wings 26 of crimping device 20 to constrict, which applies one or more radial forces to medical device 22 with force-applying surfaces 24. In some embodiments, wings 26 constrict by pivoting. As best seen in FIG. 3, while medical device 22 is operatively coupled with crimping device 20, protruding elements 34 extend from force applying surfaces 24 and at least partially, and in some embodiments fully, into openings 36 defined by struts 32 of frame 30 during at least a portion of a period (for example, the initial portion of the period) when force-applying surfaces 24 apply the forces to medical device 22. In some embodiments, the extension of protruding elements 34 through openings 36 of frame 30 during the portion of the period during which the force-applying surfaces 24 apply the forces to medical device 22 prevents the soft layer (not shown in FIGS. 1-3) of medical device 22 from protruding between struts 32 of frame 30 when medical device 22 becomes partially and/or fully crimped.

In some embodiments, preventing the soft layer of the medical device from protruding between struts 32 when medical device 22 becomes fully crimped can prevent damage that may be caused to the soft layer of medical device 22 by struts 32. Preventing the soft layer of medical device 22 from protruding between struts 32, when medical device 22 becomes partially and/or fully crimped, can also reduce the crimped profile of medical device 22, relative to if the soft layer of the device were to protrude between struts 32.

In some embodiments, a single protruding element 34 is disposed on each wing 26 of crimping device 20. In some embodiments, a plurality of protruding elements 34 is disposed on each wing 26 of crimping device 20. For example, in some embodiments, more than three and/or less than seven protruding elements 34 are disposed on each wing 26. In some embodiments, crimping device 20 includes a protruding element 34 for each opening 36 defined by struts 32 of frame 30.

In some embodiments, as medical device 22 advances through compression funnel 28, protruding elements 34 are configured to slide out of openings 36. For example, in some embodiments, protruding elements 34 are angled towards outlet 37 of compression funnel 28 and away from the pivot point of wings 26. For example, as shown in FIG. 3, protruding elements 34 define an angle α between the longitudinal axis of the respective protruding element 34 and the respective force-applying surface 24. In some embodiments, angle α is approximately 90 degrees such that the longitudinal axis of the protruding element is approximately perpendicular with the respective force-applying surface 24. In some embodiments (as shown in FIG. 3), angle α is less than approximately 90 degrees—protruding elements 34 are angled towards outlet 37 of compression funnel 28 and away from the pivot point of wing 26. In some embodiments, angle α greater than 30 degrees. When angle α is less than 90 degrees, angle α facilitates the sliding of protruding elements 34 out from openings 36 as medical device 22 is advanced through compression funnel 28 as described above.

In some embodiments, crimping device 20 is used with medical device 22 having a soft layer coupled to an inside surface of frame 30.

Figure 4:
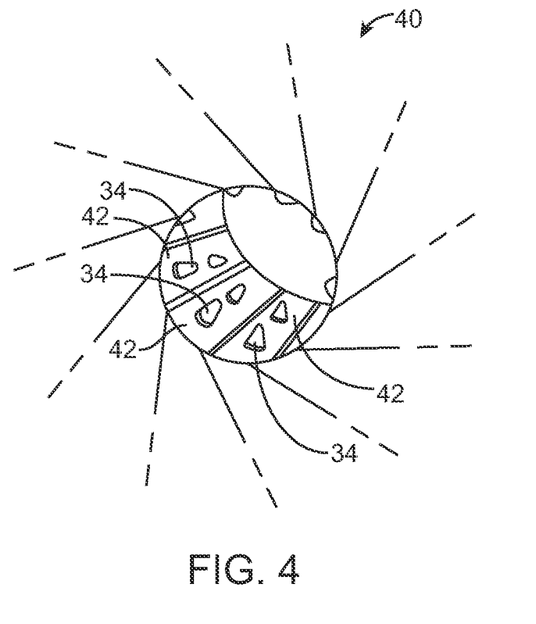
FIGS. 4-7 are schematic illustrations of a crimping device that defines a plurality of force-applying surfaces according to an embodiment.
Figure 5:
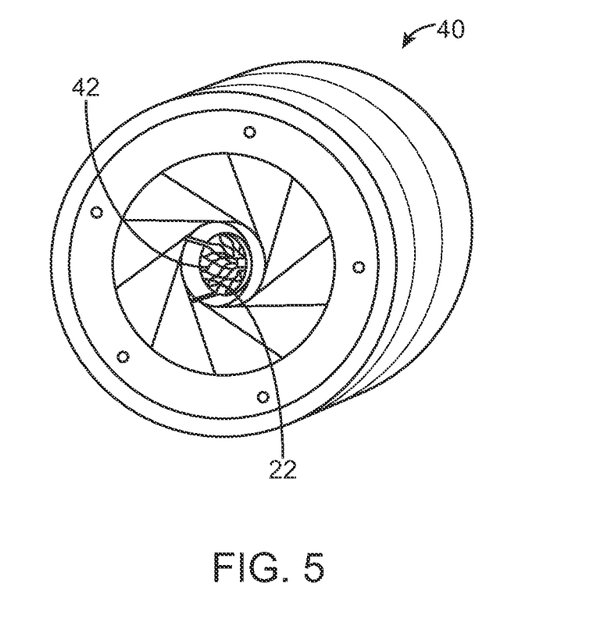
Figure 6:
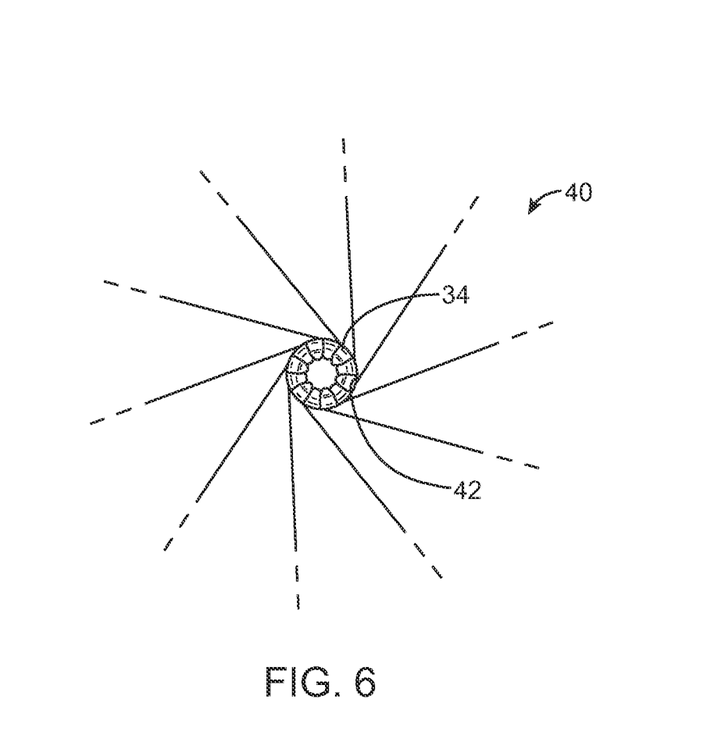
Figure 7:
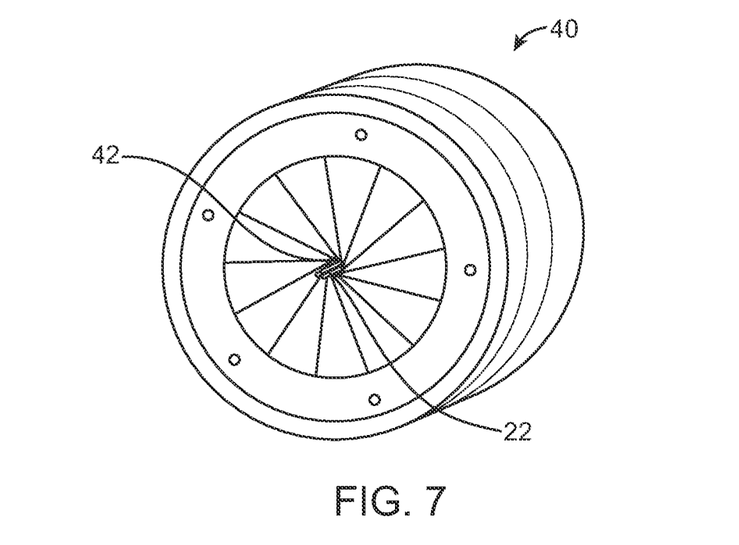

FIGS. 4-7 illustrate a crimping device 40 according to another embodiment. FIG. 4 shows crimping device 40 in the absence of medical device 22 when crimping device 40 is in an open configuration. FIG. 5 shows medical device 22 disposed inside crimping device 40 when crimping device 40 is in the open configuration. FIG. 6 shows crimping device 40 in the absence of medical device 22 when crimping device 40 is in a closed (i.e., crimped) configuration. FIG. 7 shows medical device 22 disposed inside crimping device 40 when crimping device 40 is in the closed configuration.

In some embodiments, medical device 22 can be as described above with reference to FIGS. 1-3 and comprises a soft layer (not shown) and a frame (not shown) having struts defining a plurality of openings. At least a portion of the soft layer can axially overlap with the openings of the frame.

In some embodiments, crimping device 40 defines a plurality of force-applying surfaces 42, and is configured to crimp medical device 22 by applying a radial force to the outer surface of medical device 22 with the force applying surfaces 42 as seen in the transition from FIG. 5 to FIG. 7. In some embodiments, crimping device 40 is configured such that force-applying surfaces 42 move radially toward a central axis to crimp medical device 22.

Crimping device 40 can include at least one protruding element 34 (which is generally as described hereinabove with reference to FIGS. 1-3) that is disposed on at least one force-applying surface 42 of crimping device 40. In some embodiments, a plurality of protruding elements 34 is disposed on at least some force-applying surfaces 42 of crimping device 40. When medical device 22 is operatively coupled with crimping device 40, protruding elements 34 extend from a respective inner surface 42 and at least partially, and in some embodiments fully, into the openings defined by the frame struts of medical device 22 during at least a portion of a period (for example, the initial portion of the period) during which the force-applying surfaces 42 apply the forces to medical device 22—while medical device 22 is being crimped. In some embodiments, the openings through which protruding elements 34 extend are axially overlapped with the soft layer. In some embodiments, the extension of protruding elements 34 through the openings defined by struts during the portion of the period during which the force-applying surfaces 42 apply the forces to medical device 22 prevents the soft layers of the medical device from protruding between the struts of the medical device when medical device 22 becomes partially and/or fully crimped.

In some embodiments, crimping device 40 is used with medical device 22 having a soft layer coupled to an inside surface of frame 30.

Figure 8:
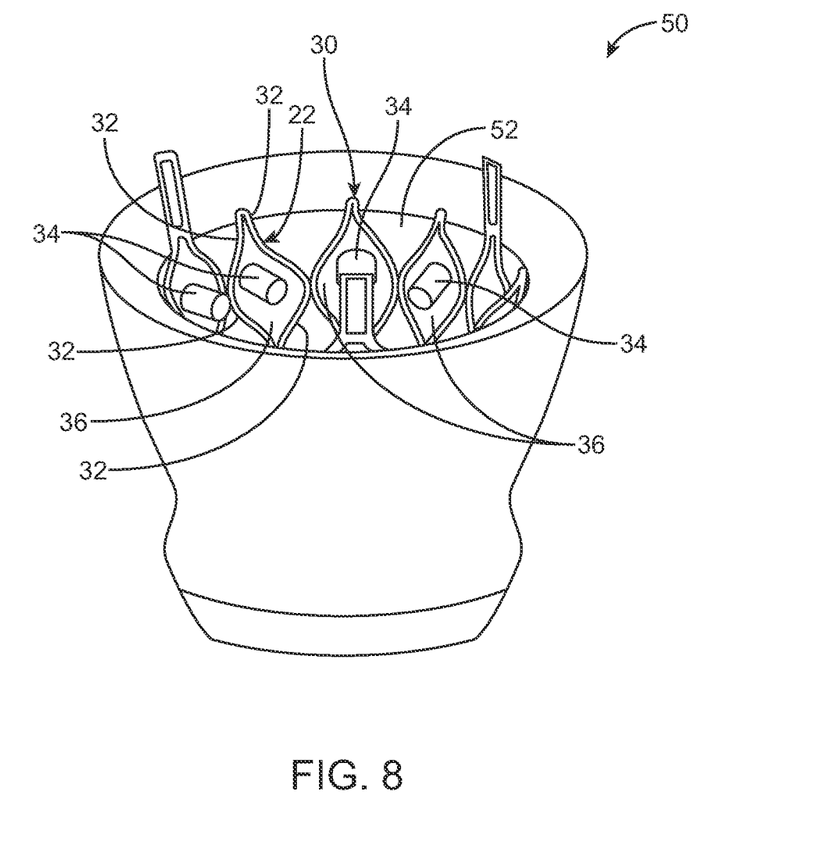
FIGS. 8 and 9 are schematic illustrations of an elastic crimping device according to an embodiment.
Figure 9:
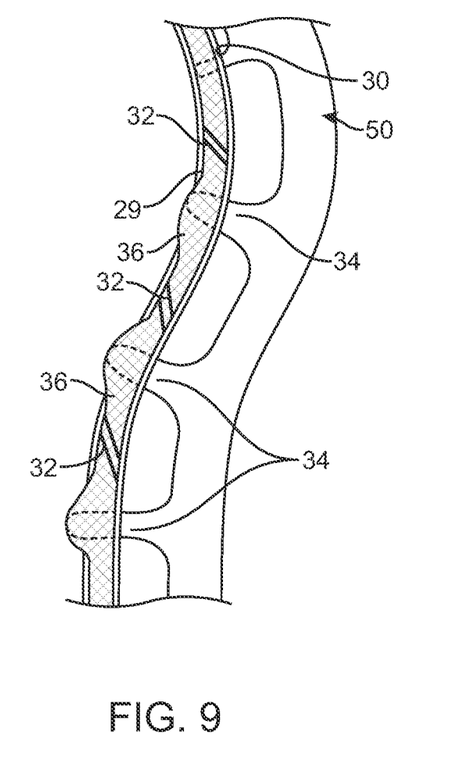

Referring to FIGS. 8 and 9, which are schematic illustrations of an elastic crimping device 50, according to an embodiment, for use with medical device 22. Medical device 22 can be constructed as described above with reference to FIGS. 1-3 and comprises a soft layer 29 (shown in FIG. 9) and a frame 30 having struts 32 defining a plurality of openings 36. At least a portion of the soft layer can axially overlap with the openings of the frame.

Crimping device 50 comprises an elastic material. Crimping device 50 is configured to be stretched around a frame 30 of medical device 22, such that the shape of inner surface 52 of crimping device 50 conforms to the shape of the outer surface of frame 30. Inner surface 52 of crimping device 50 acts as a force-applying surface and radially compresses medical device 22 by applying a radial force to the outer surface of medical device 22.

Crimping device 50 can include at least one protruding element 34 (which is generally as described above with reference to FIGS. 1-3) disposed on inner surface 52 of crimping device 50. In some embodiments, as shown in FIGS. 8 and 9, a plurality of protruding elements 34 are disposed on inner surface 52 of crimping device 50.

In some embodiments, the conformance of inner surface 52 of crimping device 50 with the outer surface of frame 30 of medical device 22 causes protruding elements 34 to at least partially, and in some embodiments fully, extend into openings 36 defined by struts 32 of frame 30. In some embodiments, these openings 36 can be axially overlapped with a soft layer of medical device 22. For example, FIG. 9 shows a cross-sectional view of crimping device 50 operatively coupled with medical device 22, in an embodiment in which frame 30 of medical device 22 defines a non-circular cross-section. As shown, the shape of elastic crimping device 50 conforms with the local shape of frame 30, and protruding elements 34 extend at least partially, and in some embodiments fully, into openings 36 defined by struts 32 of frame 30.

In some embodiments, crimping device 50 is used with medical device 22 having a soft layer coupled to an inside surface of frame 30.

Figure 10:
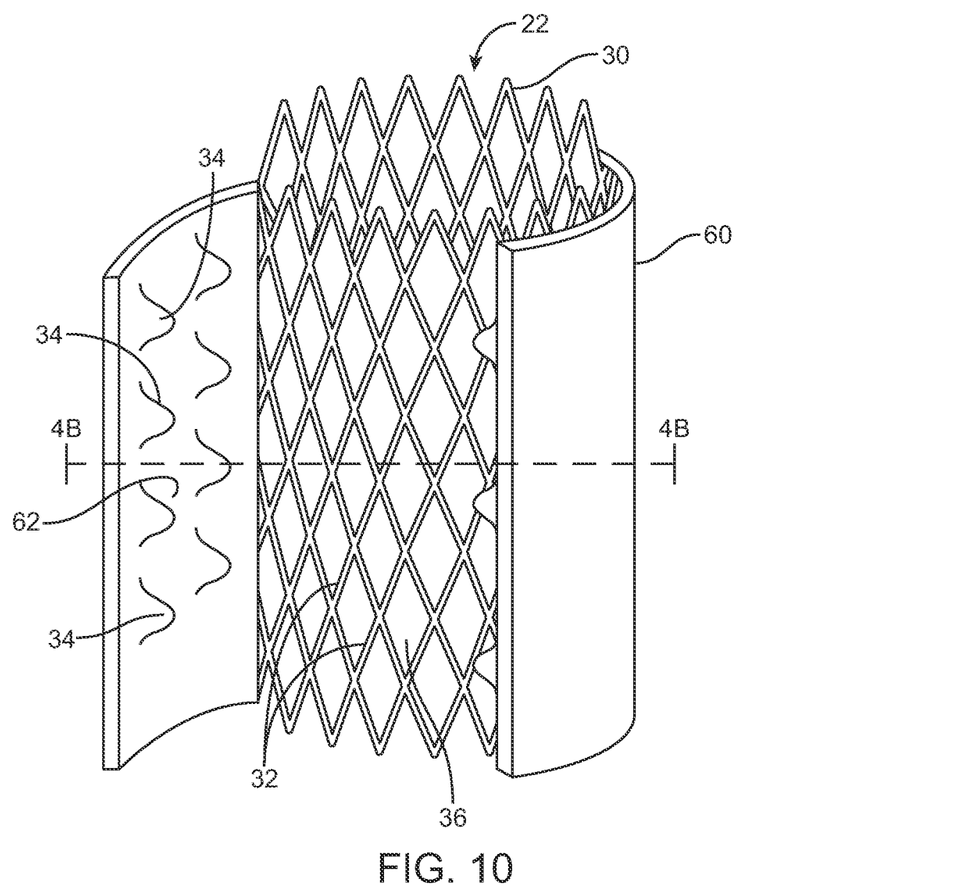
FIGS. 10 and 11 are schematic illustrations of a support member comprising protruding elements that extend from an inner surface of the support member according to an embodiment.
Figure 11:
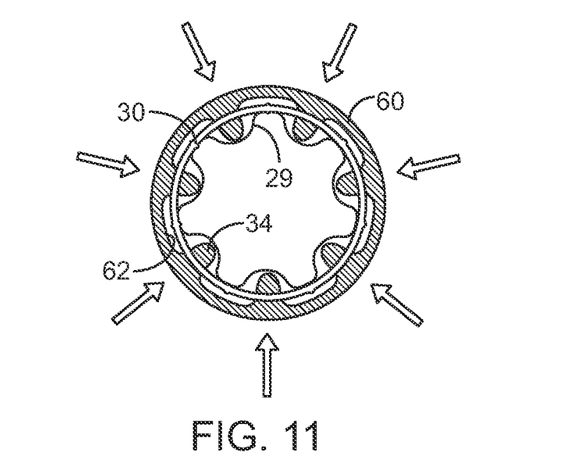

Referring to FIGS. 10 and 11, which are schematic illustrations of a support member 60 for use with a crimping device (not shown) according to an embodiment. In some embodiments, support member 60 surrounds the outside of a medical device 22, before placing the medical device into the crimping device that defines one or more force-applying surfaces that are configured to crimp medical device 22 by applying a radial force to the outer surface of medical device 22. Medical device 22 can be constructed as described above with reference to FIGS. 1-3 and comprises a soft layer 29 (shown in FIG. 11) and a frame 30 having struts 32 defining a plurality of openings 36.

In some embodiments, support member 60 can be a flexible panel or sheet that can be wrapped around medical device 22. In some embodiments, support member 60 can be an elastic tube in which medical device 22 can be inserted before operatively coupling the medical device 22 and support member 60 with the crimping device. In some embodiments, support member 60 can be a ring configured to be placed around the outside of medical device 22 before medical device 22 is placed into a crimping device.

In some embodiments, support member 60 comprises at least one protruding element 34 that extends from an inner surface 62 of support member 60. In some embodiments, a plurality of protruding elements 34 extends from inner surface 62. Protruding elements 34 can be arranged on inner surface 62 such that each protruding element 34 extends at least partially, and in some embodiments fully, into openings 36 defined by struts 32 of frame 30 during at least a portion of a period (for example, the initial portion of the period) during which the force-applying surface of the crimping device applies the force to medical device 22—while medical device 22 is being crimped. In some embodiments, the extension of protruding elements 34 into openings 36 during the portion of the period during which the force-applying surface applies the force to the medical device prevents the soft layer of the medical device from protruding between struts 32 when medical device 22 becomes partially and/or fully crimped.

In some embodiments, the crimping device may be generally similar to one of the above-described crimping devices.

In some embodiments, support member 60 is used with medical device 22 having a soft layer coupled to an inside surface of frame 30 as shown in FIG. 11.

As shown in FIG. 10, the axial length of support member 60 is substantially equal to the axial length of frame 30. In other embodiments, the axial length of support member 60 can be more or less than the axial length of frame 30. For example, the axial length of member 60 can be less than the axial length of frame 30 such that support member 60 forms a ring having a plurality of protruding elements 34.

Figure 12:
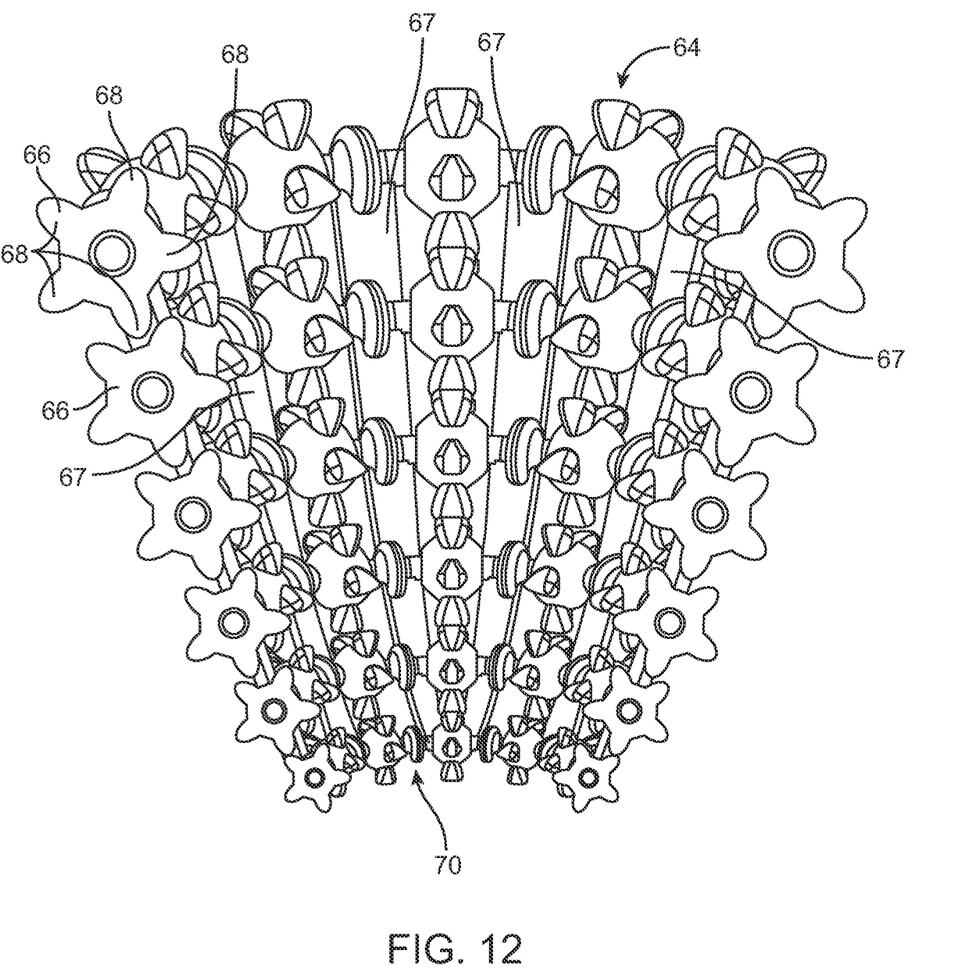
FIG. 12 is a schematic illustration of a support member having rotating cogs coupled thereto according to an embodiment.

Referring to FIG. 12, which is a schematic illustration of a compression funnel 64 according to an embodiment for use with a medical device (not shown). In some embodiments, the medical device used with funnel 64 can be constructed as described above with reference to FIGS. 1-3 and comprises a soft layer and a frame having struts defining a plurality of openings.

In some embodiments, compression funnel 64 comprises a plurality of struts 67 and a plurality of cogs 66 rotatably coupled to struts 67. Struts 67 can be circumferentially spaced apart with cogs 66 positioned between respective struts 67. Each of the plurality of rotating cogs 66 can define a plurality of teeth 68. Teeth 68 are configured to act as protruding members 34 as described above with reference to FIGS. 1-3.

In some embodiments, compression funnel 64 is conical. The narrow end of the funnel is at a distal end 70 of compression funnel 64. Distal end 70 can define an outlet for compression funnel 64. A medical device can be crimped by being pulled through the outlet at distal end 70 of compression funnel 64 thereby acting in a similar manner as the above described compression funnel 28. The inner surface of compression funnel 64 acts as a force-applying surface that applies a radial force to the medical device that compresses medical device 22. Cogs 66 can be arranged on struts 67 such that while the medical device is moved towards and through the outlet of compression funnel 64, cogs 66 rotate to cause teeth 68 to at least partially, and in some embodiments fully, extend through the openings defined by the struts of frame during at least a portion of a period (for example, the initial portion of the period) during which the force-applying surface of the funnel applies a force to the medical device. In some embodiments, the extension of teeth 68 of cogs 66 through the openings during the portion of the period during which the force-applying surface applies the force to the medical device prevents the soft layer of medical device from protruding between the struts when the medical device becomes partially and/or fully crimped.

In some embodiments, compression funnel 64 is used with a medical device having a soft layer coupled to an inside surface of the frame.

Figure 13:
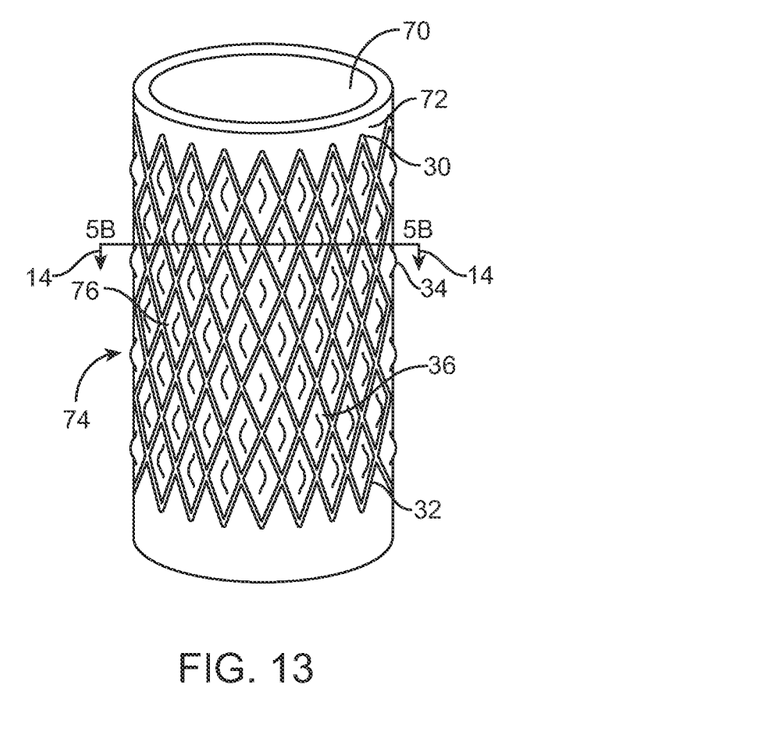
FIGS. 13-15 are schematic illustrations of a support member comprising protruding elements that extend from an outer surface of the support member according to an embodiment.
Figure 14:
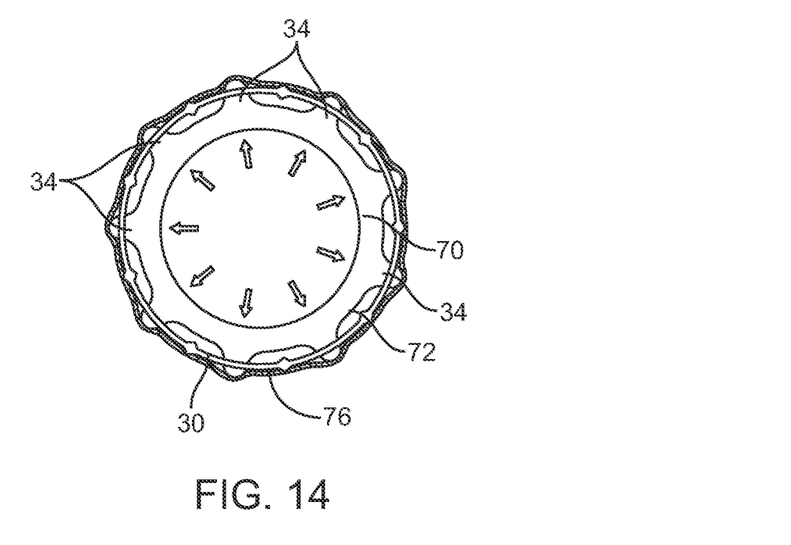
Figure 15:
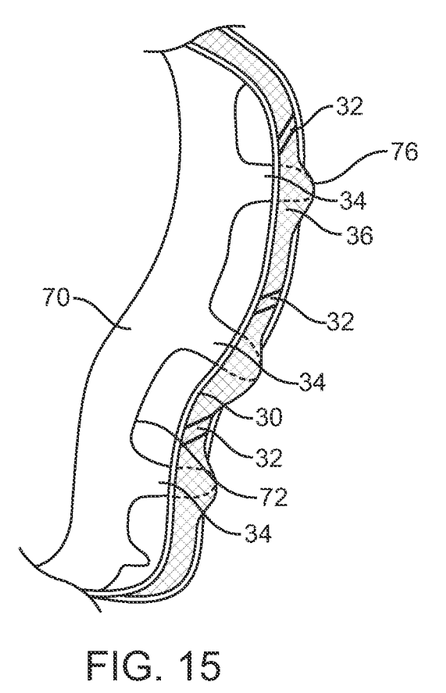

Referring now to FIGS. 13-15, which are schematic illustrations of a support member 70, according to an embodiment, for use with a crimping device. In some embodiments, support member 70 is configured to be disposed inside a medical device 74 when medical device 74 is placed inside a crimping device that defines one or more force-applying surfaces configured to crimp medical device 74 by applying a radial force to the outer surface of medical device 74. For example, the crimping device may be generally similar to one of the crimping devices described above.

In some embodiments, medical device 74 includes a soft layer 76 (e.g., a soft outer lining and/or prosthetic valve leaflets) coupled to an outside surface of frame 30 (which can be as described above with reference to FIGS. 1-3).

In some embodiments, support member 70 includes at least one protruding element 34 (which is generally as described above with reference to FIGS. 1-3) disposed on an outer surface 72 of inner compressible member 70. In some embodiments, as shown in FIGS. 13-15, a plurality of protruding elements 34 are disposed on outer surface 72 of the inner compressible member.

Protruding elements 34 can be arranged such that when medical device 74 is operatively coupled with support member 70, protruding elements 34 extend at least partially, and in some embodiments fully, into openings 36 defined by struts 32 of frame 30 of medical device 74 during at least a portion of a period (for example, the initial portion of the period) during which the force-applying surface of the crimping device applies the force to medical device 74. In some embodiments, the extension of protruding elements 34 through openings 36 of frame 30 during the portion of the period during which the force-applying surface applies the force to medical device 74 prevents soft outer layer 76 of medical device 74 from protruding between struts 32 when medical device 74 becomes partially and/or fully crimped.

In some embodiments, inner compressible member 70 comprises a balloon, a foam material, and/or a different compressible material. Although compressible member 70 as shown in FIGS. 13-15 is hollow (e.g., a hollow balloon), member 70 can be substantially solid (e.g., a solid foam device). In some embodiments, the compressibility of member 70 is such that outer surface 72 of member 70 conforms with the local shape of the inner surface of frame 30 of medical device 74 to facilitate the extension of protruding elements 34 at least partially, and in some embodiments fully, into openings 36 defined by struts 32 of frame 30. For example, FIG. 15 shows a cross-sectional view of support member 70 disposed inside medical device 74 in an embodiment in which frame 30 of medical device 74 defines a non-circular cross-section. As shown, the shape of support member 70 can conform with the local shape of frame 30, causing protruding elements 34 to at least partially, and in some embodiments fully, extend into openings 36 defined by struts 32 of frame 30.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A crimping device for use with a medical device that is to be delivered to an implantation site within a patient via a catheter-based delivery device, the medical device comprising a frame that comprises struts that define openings and comprising a soft layer coupled to the frame, the crimping device comprising:

a force-applying surface configured to compress the entire medical device to a compressed delivery configuration for loading within the catheter-based delivery device by applying a force to an outer surface of the medical device; and at least one protruding element extending from the force-applying surface and arranged to least partially extend into one of the openings defined by the struts while the medical device is being crimped, wherein the extension of the at least one protruding element at least partially into one of the openings prevents at least a portion of the soft layer of the medical device from protruding between struts of the frame of the medical device while the device is being crimped.

2. The crimping device according to claim 1, wherein the at least one protruding element comprises a plurality of protruding elements arranged to at least partially protrude into respective openings defined by the struts while the medical device is being crimped.

3. The crimping device according to claim 1, wherein the at least one protruding element is configured to slide out of the opening defined by the struts as the medical device is moved with respect to the crimping device.

4. The crimping device according to claim 3, wherein an angle between a longitudinal axis of the at least one protruding element and the force-applying surface is greater than about 30 degrees.

5. The crimping device according to claim 1, wherein the at least one protruding element is rigid.

6. The crimping device according to claim 1, wherein the force-applying surface comprises a plurality of force-applying surfaces.

7. The crimping device according to claim 6, wherein the at least one protruding element comprises a plurality of protruding elements that are disposed on each force-applying surface.

8. The crimping device according to claim 1, wherein the force-applying surface is shaped to conform to a shape of the outer surface of the medical device.

9. The crimping device according to claim 8, wherein the force-applying surface is elastic.

10. The crimping device according to claim 1, further comprising a rotatable cog having a tooth, the tooth defining the at least one protruding element.

11. The crimping device according to claim 10, wherein the crimping device is configured to crimp the medical device as the medical device is moved with respect to the crimping device, and wherein movement of the medical device with respect to the crimping device rotates the cog.

12. A crimping system for use with a medical device that is to be delivered to an implantation site within a patient via a catheter-based delivery device, the medical device comprising a frame that comprises struts that define openings and comprising a soft layer coupled to the frame, the crimping system comprising:

a crimping device comprising a force-applying surface configured to compress the entire medical device to a compressed delivery configuration for loading within the catheter-based delivery device by applying a force to an outer surface of the medical device; and a support member configured to be placed about a periphery of the medical device between the crimping device and the medical device while the force-applying surface of the crimping device applies a force to the outer surface of the medical device, the support member comprising at least one protruding element extending from an inner surface of the support member and arranged to at least partially extend into one of the openings defined by the struts while the crimping device crimps the medical device, wherein the at least one protruding element is configured to at least partially extend into one of the openings to prevent at least a portion of the soft layer of the medical device from protruding between struts of the frame of the medical device while the device is being crimped.

13. The crimping system according to claim 12, wherein the at least one protruding element comprises a plurality of protruding elements configured to at least partially extend into respective openings defined by the struts.

14. A crimping system for use with a medical device that is to be delivered to an implantation site within a patient via a catheter-based delivery device, the medical device comprising a frame that comprises struts that define openings and comprising a soft layer coupled to the frame, the crimping system comprising:

a crimping device comprising a force-applying surface configured to compress the entire medical device to a compressed delivery configuration for loading within the catheter-based delivery device by applying a force to an outer surface of the medical device, and a support member configured to be placed inside the medical device while the force-applying surface of the crimping device applies a force to the outer surface of the medical device, the support member comprising at least one protruding element that extends from an outer surface of the support member and that is arranged to at least partially extend into one of the openings defined by the struts while the crimping device crimps the medical device, wherein the at least one protruding element is configured to at least partially extend into one of the openings to prevent at least a portion of the soft layer of the medical device from protruding between struts of the frame of the medical device while the medical device is being crimped.

15. The crimping system according to claim 14, wherein the support member is configured such that a shape of the outer surface of the support member conforms to a shape of the frame of the medical device.

16. The crimping system according to claim 14, wherein the support member comprises a balloon.

17. The crimping system according to claim 14, wherein the support member comprises a solid foam member.

* * * * *